(12) United States Patent
Lan

(10) Patent No.: US 10,377,950 B2
(45) Date of Patent: Aug. 13, 2019

(54) BRANCHED ORGANOSILICON MATERIAL, AND METHOD FOR MANUFACTURING LIQUID CRYSTAL DISPLAY PANELS

(71) Applicant: Shenzhen China Star Optoelectronics Technology Co., Ltd., Shenzhen (CN)

(72) Inventor: Song Lan, Shenzhen (CN)

(73) Assignee: SHENZHEN CHINA STAR OPTOELECTRONICS TECHNOLOGY CO., LTD., Shenzhen (CN)

( * ) Notice: Subject to any disclaimer, the term of this patent is extended or adjusted under 35 U.S.C. 154(b) by 63 days.

(21) Appl. No.: 14/897,783

(22) PCT Filed: Sep. 1, 2015

(86) PCT No.: PCT/CN2015/088752
§ 371 (c)(1),
(2) Date: Oct. 24, 2017

(87) PCT Pub. No.: WO2017/031775
PCT Pub. Date: Mar. 2, 2017

(65) Prior Publication Data
US 2018/0057745 A1 Mar. 1, 2018

(30) Foreign Application Priority Data
Aug. 25, 2015 (CN) .......................... 2015 1 0526256

(51) Int. Cl.
*A61K 8/58* (2006.01)
*C09K 19/56* (2006.01)
(Continued)

(52) U.S. Cl.
CPC ............ *C09K 19/56* (2013.01); *C07F 7/1804* (2013.01); *C08G 77/045* (2013.01); *C08G 77/26* (2013.01);
(Continued)

(58) Field of Classification Search
CPC ....................................................... G02F 1/13
See application file for complete search history.

(56) References Cited

U.S. PATENT DOCUMENTS 3,574,670 A * 4/1971 Curry .................... C07F 7/1804
427/247
5,851,840 A * 12/1998 Sluka ...................... A61L 27/34
436/525
(Continued)

FOREIGN PATENT DOCUMENTS

CN 102007447 A 4/2011
CN 102516916 A 6/2012
(Continued)

OTHER PUBLICATIONS

Deng et al., "A Concerted H-Bonding Self-Assembly-Based Approach to Ladder Poly(silsesquioxane)," Macromolecular Chemistry and Physics, (2006), vol. 207, No. 4, pp. 404-411.
(Continued)

*Primary Examiner* — Chanceity N Robinson (57) ABSTRACT

Disclosed is a branched organosilicon material, and a method of manufacturing a liquid crystal display panel with the branched organosilicon material, without use of an alignment film. In addition, a liquid crystal display panel thus manufactured is further disclosed.

16 Claims, 2 Drawing Sheets

(51) Int. Cl.

| | | |
|---|---|---|
| *C07F 7/18* | (2006.01) | |
| *C08G 77/04* | (2006.01) | |
| *C08G 77/26* | (2006.01) | |
| *G02F 1/1337* | (2006.01) | |
| *C08L 83/04* | (2006.01) | |
| *C08L 83/08* | (2006.01) | |
| C08G 77/00 | (2006.01) | |
| G02F 1/1341 | (2006.01) | |
| G02F 1/1368 | (2006.01) | |

(52) U.S. Cl.
CPC .............. *C08L 83/04* (2013.01); *C08L 83/08* (2013.01); *G02F 1/133788* (2013.01); *C08G 77/80* (2013.01); *G02F 1/1341* (2013.01); *G02F 1/1368* (2013.01); *G02F 2001/13415* (2013.01); *G02F 2001/133742* (2013.01)

(56) References Cited

U.S. PATENT DOCUMENTS

| 8,558,972 B2 | 10/2013 | Asaoka et al. |
|---|---|---|
| 2014/0342086 A1 | 11/2014 | Ibn-Elhaj et al. |
| 2015/0085236 A1 | 3/2015 | Kanehiro et al. |
| 2018/0044239 A1 | 2/2018 | Menz et al. |

FOREIGN PATENT DOCUMENTS

| JP | 1995260790 A | 10/1995 |
|---|---|---|
| JP | 1996034955 A | 2/1996 |
| JP | 2915803 B2 * | 7/1999 |
| JP | 2915803 B2 | 7/1999 |
| JP | 2005-97150 A | 4/2005 |
| JP | 2006-131850 A | 5/2006 |
| JP | 2014028788 A | 2/2014 |
| JP | 2014196540 A | 10/2014 |
| RU | 2177484 C1 | 12/2001 |

OTHER PUBLICATIONS

Ren et al., "Ladder polysilsesquioxane for wide-band semiconductors: synthesis, optical properties and doped electrophorescent device," Journal of Materials Chemistry, (2011), vol. 21, No. 30, pp. 11306-11311.

Notification of Transmittal of the International Search Report and the Written Opinion of the International Searching Authority (Forms PCT/ISA/220, PCT/ISA/210, and PCT/ISA/237) dated Apr. 29, 2016, by the State Intellectual Property Office of People's Republic of China in corresponding International Application No. PCT/CN2015/088752. (12 pages).

Office Action dated May 19, 2017, by the State Intellectual Property Office of People's Republic of China in corresponding Chinese Patent Application No. 201510526256.0 (11 pages).

English abstract of DENG et al., "Concerted H-Bonding Template Synthesis of an Ordered Ladder Polysilsesquioxane," Chinese Journal of Polymer Science, (Sep. 2006), vol. 24, No. 5, pp. 539-544. (2 pages).

Kullin Deng, A Concerted H-Bonding Self-Assembly-Based Approach to Ladder Poly (sisesquoxane), Macromolecular Chemistry and Physics, 2006, pp. 404-411.

Kui-lin Deng, Concerted H-Bonding Template Synthesis of an Ordered Ladder Polysilsesquioxane, Chinese Journal of Polymer Sciencw, 2006, pp. 539-544, vol. 24, No. 5.

Zhongjie Ren, Ladder polysilsesquioxane for wide-band semiconductors: synthesis, optical properties and doped electrophosphorescent device, Journal of Materials Chemistry, 2011, pp. 11306-11311, vol. 21, No. 30.

* cited by examiner

BRANCHED ORGANOSILICON MATERIAL, AND METHOD FOR MANUFACTURING LIQUID CRYSTAL DISPLAY PANELS

CROSS-REFERENCE TO RELATED APPLICATIONS

The present application claims the priority of Chinese patent application CN 201510526256.0, entitled "A branched organosilicon material, and method for manufacturing liquid crystal display panels" and filed on Aug. 25, 2015, the entirety of which is incorporated herein by reference.

FIELD OF THE INVENTION

The present disclosure relates to the field of display technologies, and in particular, to a branched organosilicon material. The organosilicon material can allow an LC to be vertically aligned. The present disclosure further relates to use of the organosilicon material.

BACKGROUND OF THE INVENTION

On a CF substrate and a TFT substrate of a liquid crystal display device (LCD), a layer of film material, named alignment film (commonly polyimide (PI) material) is provided, mainly to align liquid crystal molecules in a certain direction. This kind of alignment films can be substantially divided into friction alignment PI materials and light alignment PI materials. However, both of the alignment materials have their own shortcomings. First, friction alignment is easy to cause dust particles, electrostatic residues, brush marks and other problems that reduce a process yield. The light alignment materials, although can avoid these problems, are subject to limited material properties, inferior heat resistance and aging resistance, and weak ability of anchoring LC molecules, which affect the quality of the panel. Moreover, PI materials, of high polarity and high water absorption per se, can be easily deteriorated during storage and transportation thereof, causing inhomogeneous alignment. In addition, PI materials are expensive, and a filming procedure thereof on a TFT-LCD is relatively complex, resulting in increased costs of the panel.

The present disclosure aims to provide a new material and a new method, whereby PI films can be saved in the TFT-LCD while the liquid crystal molecules can still be aligned. This will not only greatly simplify a manufacturing procedure of the TFT-LCD, but also reduce manufacturing costs of the TFT-LCD.

SUMMARY OF THE INVENTION

In view of the shortcomings in the prior art, the present disclosure provides a branched organosilicon material, which, while being used in a TFT-LCD, can allow liquid crystal molecules to be aligned without a PI film, thereby significantly reducing manufacturing costs of a panel.

According to one aspect of the present disclosure, a branched organosilicon material is provided, with its molecular formula shown in formula I, formula I wherein, $R^1$ is directly connected to a silicon atom, while $R^2$ is connected to a silicon atom via an oxygen atom, two adjacent silicon atoms being connected via an oxygen atom;

wherein n is an integer in the range from 2 to 15;

wherein $R^2$ is a $C_1$-$C_5$ alkyl; and wherein $R^1$ is a group containing 10-30 carbon atoms, optionally including or not including a group selected from —$CR^3$=$CR^3$—, —C≡C—, $C_6$-$C_{20}$ arylene, $C_3$-$C_{15}$ cycloalkylene, —CONH—, and —COO—, one or more H atoms of $R^1$ optionally being substituted or not being substituted by heteroatoms, which can be halogen atoms, nitro groups, alkoxy groups, or the like, wherein $R^3$ is hydrogen or a $C_1$-$C_3$ alkyl.

According to the present disclosure, the structure of the organosilicon material mainly includes two parts: a head group A and a tail group B with a plurality of chains. A refers to $Si_nO_{2n+1}$, and is substantially a branched structure; while B refers to $R^1_n R^2_{n+2}$, i.e., a structure with a plurality of branches. Due to the unique structure of —Si—O—, the branched organosilicon small molecular material of the present disclosure has the characteristics of both an organic material and an inorganic material. On the one hand, it is provided with low surface tension and low surface energy; and on the other hand, because the bond energy of —Si—O— (462 kJ/mol) is higher than that of —C—C— (347 kJ/mol), the temperature resistance and oxidation resistance of the material are increased. In addition, —Si—O— is also a polar anchoring group, capable of anchoring other materials.

According to one specific embodiment of the branched organosilicon material of the present disclosure, n is preferably an integer in the range from 2 to 10, and more preferably an integer in the range from 2 to 6. Preferably, $R^2$ is methyl, ethyl, or propyl. Preferably, $R^1$ contains a group selected from —$CR^3$=$CR^3$—, —C≡C—, phenylene, $C_3$-$C_6$ cycloalkylene, —CONH—, and —COO—. Meanwhile, when the phenyl or cycloalkylene is included, the H atoms in the phenyl or cycloalkylene are optionally substituted or not substituted with halogen atoms. $R^3$ is hydrogen, methyl, or ethyl.

According to one preferred embodiment of the present disclosure, in the branched organosilicon material, $R^2$ is methyl, ethyl, or propyl; and $R^1$ is selected from the following groups:

—(CH$_2$)$_2$—CONH—CONH—C$_6$H$_{13}$,

—(CH$_2$)$_2$—CONH—HC=CH—COO—C$_8$H$_{17}$,

—(CH$_2$)$_2$—CONH—C$_4$H$_8$—COO—C$_6$H$_{13}$,

—(CH$_2$)$_2$—CONH—C$_5$H$_{11}$, and

—(CH$_2$)$_2$—CONH—C$_5$H$_{11}$.

According to one preferred embodiment of the present disclosure, when n is 2, 3, or 4, the organosilicon material is shown in formula II, III, or IV:

formula II formula III formula IV wherein, when n increases, the —OR² in the formula of the organosilicon material is continuously substituted by —OSiR¹ (OR²)₂.

According to the present disclosure, the branched organosilicon material has low surface tension and low surface energy, and meanwhile high temperature resistance and oxidation resistance. The silicon oxygen bond contained in the organosilicon material can interact with other atoms, and play an anchoring role.

The branched organosilicon material of the present disclosure can be prepared by controlled hydrolysis performed on a silicon compound shown in general formula R¹Si(OR²)₃, wherein, the silicon compound shown in general formula R¹Si (OR²)₃ can be prepared through, for example, a condensation procedure.

According to another aspect of the present disclosure, a method for manufacturing a liquid crystal display panel is provided, comprising:

step 1): providing a cell body including a first substrate and a second substrate, neither the first substrate nor the second substrate having an alignment film;

step 2): adding a reactive monomer and the above branched organosilicon material into a liquid crystal to obtain a mixed solution;

step 3): dropwise adding the mixed solution between the first substrate and the second substrate in the cell body, at which time the branched organosilicon material enables the liquid crystal to be vertically aligned on a surface of the first substrate and a surface of the second substrate;

step 4): applying a voltage to deflect the liquid crystal, followed by polymerization of the reactive monomer on the surface of the first substrate and the surface of the second substrate, to anchor the liquid crystal; and step 5): releasing the voltage to obtain the liquid crystal display panel.

According to one specific embodiment of the method of the present disclosure, in step 2), the mixed solution contains 0.1-5 wt % of the branched organosilicon material. The structure of the organosilicon material mainly includes two parts: a head group A and a tail group B with a plurality of chains. A refers to $Si_nO_{2n+1}$, and is substantially a branched structure. Formation of the head group by a plurality of silicon-oxygen groups can enhance adhesion of a polar group on the surface of the substrate and enhance an anchoring effect therebetween. The —Si—O— is a polar anchoring group, the main function of which is to anchor the head group on the surface of the substrate. B refers to $R^1_n R^2_{n+2}$, i.e., a structure with a plurality of branches. The tail group mainly functions as a three-dimensional obstacle, to vertically align the liquid crystal molecules. The design of multiple tail groups can improve an effect of vertical alignment against LC molecules.

According to another specific embodiment of the method of the present disclosure, in step 2), the reactive monomer comprises at least one selected from a group consisting of epoxy resin and fatty amine epoxy curing agent combination, acrylates and derivatives thereof, methyl acrylate and derivatives thereof, styrene and derivatives thereof. The reactive monomer is a commonly used radiation-polymerizable compound in the polymer field, and will not be described in detail herein. The mixed solution contains 0.01-0.1 wt % of the reactive monomer.

According to another specific embodiment of the method of the present disclosure, in step 4), the polymerization is a radiation polymerization, wherein the light source used for the radiation polymerization is a UV light of 313 nm. Radiation dose is in the range from 0.1 to 1 mW/cm². Preferably, the voltage applied is in the range from 15 to 25 V.

According to another specific embodiment of the method of the present disclosure, in step 1), the first substrate and the second substrate are respectively a color filter (CF) substrate and a thin film transistor (TFT) substrate. Depending on different materials of the substrates on which —Si—O— is located, the action mechanisms between the —Si—O— and the substrates are different. The action mechanisms mainly include the following two types: i) the interaction mechanism between —Si—O— and ITO is that a lone pair of electrons in the oxygen atom in —Si—O— are hybridized with an empty p orbital or d orbital in an indium atom (configuration of extra-nuclear electrons: In:[Kr] 4d10 5s2 5p1) or a tin atom (configuration of extra-nuclear electrons: Sn:[Kr] 4d10 5s2 5p2) in the ITO on a surface of the substrate, so as to achieve combination therebetween via a coordination bond; ii) the interaction mechanism between —Si—O— and SiNx is that the oxygen atom in —Si—O— interacts with the nitrogen atom in SiNx.

According to the present disclosure, the branched organosilicon material has the characteristics of both an organic material and an inorganic material, i.e., low surface tension and low surface energy, and high temperature resistance and high oxidation resistance. A has a plurality of —Si—O— groups, primarily enhancing the anchoring action with the substrate. B's structure of a plurality of branches mainly improves the effect of LC vertical alignment.

According to the method of manufacturing a liquid crystal display panel provided in the present disclosure, the branched organosilicon material is used to replace a PI alignment film in the TFT-LCD, to save a PI manufacturing procedure, thereby remarkably simplifying a manufacturing process of the liquid crystal display panel, and reducing the manufacturing costs thereof.

According to another aspect of the present disclosure, a liquid crystal display panel is further provided, comprising: a first substrate, a second substrate, a liquid crystal, a polymer, and the above-described branched organosilicon material.

According to the liquid crystal display panel provided in the present disclosure, the liquid crystal can be aligned in a certain direction, wherein the polymer is obtained by polymerization of the reactive monomer.

The liquid crystal of the present disclosure is a commonly used one in the art and will not be described in detail herein.

According to one specific embodiment of the liquid crystal display panel of the present disclosure, the first substrate is a color filter substrate and the second substrate is a thin film transistor substrate. In another specific embodiment, the first substrate and the second substrate are free of alignment films.

According to the new branched organosilicon material provided in the present disclosure, it has a structure of a plurality of silicon-oxygen groups and a plurality of branched chains. When the branched organosilicon material is used in the LCD field, on the one hand, it can form an anchor effect with the substrate, and the effect of the plurality of branches can improve the vertical alignment of the liquid crystal. According to the branched organosilicon material provided in the present disclosure, it can be used for manufacture of the liquid crystal display panel, without an alignment film.

DETAILED DESCRIPTION OF THE EMBODIMENTS

The present disclosure will be further described in the following with reference to the accompanying drawings and specific embodiments, which are not to be construed as limiting the present disclosure.

Figure 1:
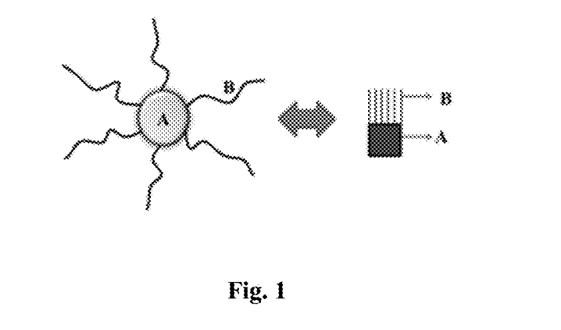
FIG. 1 schematically shows the structure of a branched organosilicon material according to the present disclosure.

FIG. 1 schematically shows the structure of a branched organosilicon material according to the present disclosure. As shown in FIG. 1, the structure of the branched organosilicon material mainly includes a head group A and a tail group B with a plurality of chains. A refers to $Si_nO_{2n+1}$, and is substantially a branched structure; and B refers to $R^1{}_n R^2{}_{n+2}$, i.e., a structure with a plurality of chains.

Figure 2:
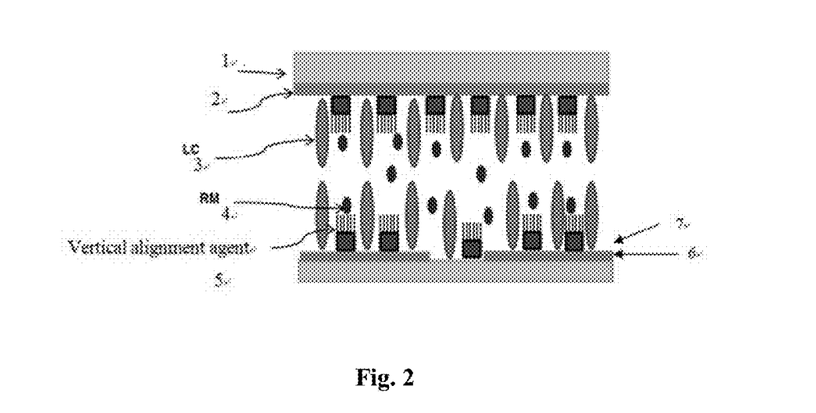
FIG. 2 schematically shows action of the branched organosilicon material according to one embodiment of the present disclosure.

FIG. 2 schematically shows action of the branched organosilicon material according to one embodiment of the present disclosure, wherein, a first substrate 1 and a second substrate 6 are respectively a CF substrate and a TFT substrate. Indium tin oxide (ITO) layers 2 and 7 are respectively arranged on the first substrate 1 and the second substrate 6, wherein the ITO only partially covers the second substrate 6. A reactive monomer 4, a branched organosilicon material 5, acid a liquid crystal 3 are disposed between the first substrate 1 and the second substrate 6. And liquid crystal molecules are vertically aligned under the action of the branched organosilicon material 5. The organosilicon material 5 functions as a vertical alignment agent.

Figure 3:
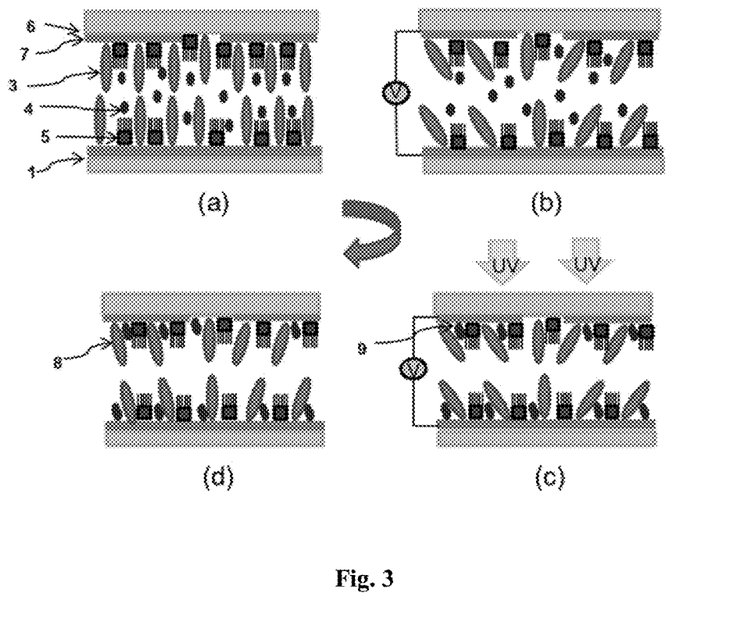
FIG. 3 is flow chart for manufacturing a liquid crystal display panel according to one embodiment of the present disclosure.

FIG. 3 is a flow chart for manufacturing a liquid crystal display panel according to one embodiment of the present disclosure. a) A cell body including the first substrate 1 and the second substrate 6 is provided, neither the first substrate nor the second substrate having an alignment film; the reactive monomer 4 and the branched organosilicon material 5 are added into the liquid crystal 3, to prepare a mixed solution; the mixed solution is dropwise added between the first substrate 1 and the second substrate 6 in the cell body, at which time the branched organosilicon material 5 enables the liquid crystal 3 to be vertically aligned on a surface of the first substrate 1 and a surface of the second substrate 6. b) A voltage of 20 V is applied to deflect the liquid crystal. c) The reactive monomer 4 is polymerized on the surface of the first substrate 1 and the surface of the second substrate 6 under radiation of UV light with a wavelength of 313 nm (0.5 mW/cm$^2$), to obtain a polymer 9, which anchors the liquid crystal. d) The voltage is released to obtain the liquid crystal display panel. The liquid crystal 3 in the panel has a pretilt angle 8. Therein, the reactive monomer used is methyl acrylate. The mixed solution contains 0.05 wt % of the reactive monomer, and 3 wt % of the branched organosilicon material. In the branched organosilicon material used, n is 3, and $R^1$ and $R^2$ are respectively —(CH$_2$)$_2$—CONN—HC=CH—COO—C$_8$H$_{17}$ and methyl. It will be appreciated by those skilled in the art that other types and amounts of reactive monomers, other types and amounts of branched organosilicon materials, other voltages and radiation doses within the limits of the present disclosure can be used to achieve the present disclosure, and obtain the liquid crystal display panel also.

Figure 4:
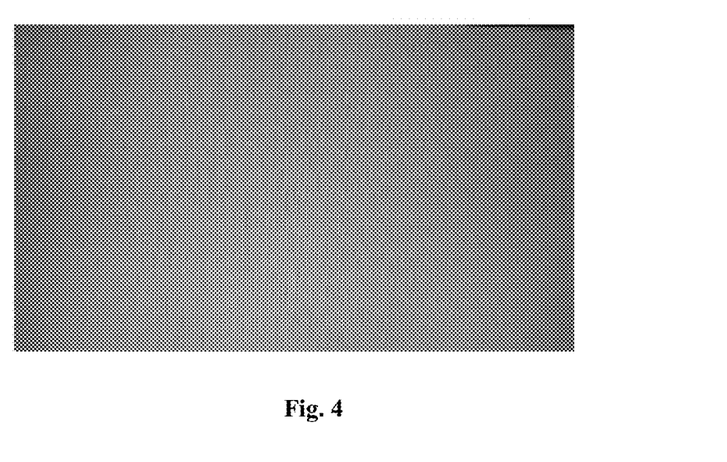
FIG. 4 schematically shows a liquid crystal display panel according to one embodiment of the present disclosure.

FIG. 4 shows the liquid crystal display panel obtained in accordance with the present disclosure, in which liquid crystal molecules are normally aligned and screens can be normally displayed. This indicates that the branched organosilicon material is capable of vertically aligning the liquid crystal molecules, such that the liquid crystal display panel can be manufactured without use of an alignment film.

The following examples are to show synthesis of two organosilicon materials. Other organosilicon materials can also be synthesized with reference of the following procedures.

Example 1

Small linear organosilicon molecules were synthesized, as shown in route 1),

1)

formula i)   formula ii)

formula iv)   formula iv)

wherein the molar ratio of the compound shown in formula i) and the compound shown in formula ii) was in the range from 1:1 to 1:1.4, preferably being 1:1.2; the temperature for reaction between the compound shown in formula i) and the compound shown in formula ii) was in the range from 20° C. to 60° C., preferably being 50° C.; and the reaction time was in the range from 1 h to 5 h, preferably being 4 h.

The reaction temperature for synthesis of the compound shown in formula iv) with the compound shown in formula iii) and amylamine was in the range from 60° C. to 90° C., preferably being 80° C.; and the reaction was performed in 1 h to 5 h, preferably 3 h.

The $H^1$-NMR data of the compound shown in formula iv) were as follows: δ: 0.96 (3H), 1.33 (2H), 1.29 (2H), 1.59 (2H), 3.20 (2H), 8.0 (1H), 8.13 (2H), 7.69 (2H), 3.55 (9H), 3.2 (2H), and 0.88 (2H).

The silicon compound shown in formula iv) was then hydrolyzed, to obtain the branched organosilicon material of the present disclosure, as shown in route 3),

3)

wherein, $R^1$ was and R2 was methyl, i.e., was the compound shown in formula iv).

When the organosilicon material with n=2 was prepared, the molar ratio of the compound of formula iv) to $H_2O$ was in the range from 1:1.1 to 1:1.5, preferably being 1:1.3, and the reaction temperature was 50° C. A small amount of $H_2SO_4$ was added to promote hydrolysis, to obtain the organosilicon material with n=2.

The $H^1$-NMR data were as follows: δ: 0.96 (6H), 1.33 (4H), 1.29 (8H), 1.59 (4H), 3.20 (4H), 8.0 (4H), 8.13 (4H), 7.69 (4H), 3.55 (12H), 3.2 (4H), and 0.88 (4H).

It will be appreciated by those skilled in the art that by controlling the molar ratio of the compound shown in formula iv) to $H_2O$ and other conditions, organosilicon materials with other values of n can be obtained.

Example 2

Small linear organosilicon molecules were synthesized, as shown in route 2), wherein the molar ratio of the compound shown in formula i) and the compound shown in formula v) was in the range from 1:1 to 1:1.4, preferably being 1:1.2; the temperature for reaction between the compound shown in formula i) and the compound shown in formula v) was in the range from 20° C. to 60° C., preferably being 40° C.; and the reaction time was in the range from 1 h to 5 h, preferably being 3 h.

The molar ratio of the compound shown in formula vi) to n-octanol was 1:1, in which 1.1×$SOCL_2$ was added, followed by a one-hour reaction.

The $H^1$-NMR data of the compound shown in formula vii) as obtained, were as follows: δ: 0.96 (3H), 1.33 (2H), 1.29 (8H), 1.57 (2H), 4.15 (2H), 3.55 (9H), 8.0 (1H), 3.0 (2H), 0.84 (2H), 7.49 (1H), and 6.95 (1H).

2)

The silicon compound shown in formula vii) was then hydrolyzed, to obtain the branched organosilicon material of the present disclosure, as shown in route 3), wherein $R^2$ was methyl, and $R^1$ was —$(CH_2)_2$—CONH—HC=CH—COO—$C_8H_{17}$.

When the organosilicon material with n=2 was manufactured, the molar ratio of two reaction materials was in the range from 1:1.1 to 1:1.5, preferably being 1:1.2, and the reaction temperature was 50° C. A small amount of $H_2SO_4$ was added to promote hydrolysis.

The $H^1$-NMR data were as follows: δ: 0.96 (6H), 1.33 (4H), 1.29 (16H), 1.57 (4H), 4.15 (4H), 3.55 (12H), 1.93 (12H), 8.0 (2H), 3.0 (4H), and 0.84 (4H).

It will be appreciated by those skilled in the art that by controlling the molar ratio of the compound shown in formula iv) to $H_2O$ and other conditions, organosilicon materials with other values of n can be obtained.

2)

It should be noted that the above examples are only used to explain, rather than to limit the present disclosure in any manner. Although the present disclosure has been discussed with reference to preferable examples, it should be understood that the terms and expressions adopted are for describing and explaining instead of limiting the present disclosure. The present disclosure can be modified within the scope of the claims, or can be amended without departing from the scope or spirits of the present disclosure. Although the present disclosure is described with specific methods, materials, and examples, the scope of the present disclosure herein disclosed should not be limited by the particularly disclosed examples as described above, but can be extended to other methods and uses having the same functions.

The invention claimed is:

1. A branched organosilicon material, with its molecular formula shown in formula I,

$$Si_nO_{2n+1}R^1{}_nR^2{}_{n+2},\quad \text{formula I}$$

wherein $R^1$ is directly connected to a silicon atom, while $R^2$ is connected to a silicon atom via an oxygen atom, two adjacent silicon atoms being connected via an oxygen atom;

wherein n is an integer in the range from 2 to 15;

wherein $R^2$ is a $C_1$-$C_5$ alkyl; and wherein $R^1$ is selected from the following groups:

2. The branched organosilicon material according to claim 1, wherein n is an integer in the range from 2 to 10; wherein $R^2$ is methyl, ethyl, or propyl.

3. The branched organosilicon material according to claim 1, wherein n is an integer in the range from 2 to 6; wherein $R^2$ is methyl, ethyl or propyl.

4. The branched organosilicon material according to claim 1, wherein when n is 2, 3, or 4, the organosilicon material is shown in formula II, III, or IV:

5. A method for manufacturing a liquid crystal display panel, comprising:

step 1): providing a cell body including a first substrate and a second substrate, neither the first substrate nor the second substrate having an alignment film;

step 2): adding a reactive monomer and a branched organosilicon material into a liquid crystal to obtain a mixed solution;
step 3): dropwise adding the mixed solution between the first substrate and the second substrate in the cell body, at which time the branched organosilicon material enables the liquid crystal to be vertically aligned on a surface of the first substrate and a surface of the second substrate;
step 4): applying a voltage to deflect the liquid crystal, followed by polymerization of the reactive monomer on the surface of the first substrate and the surface of the second substrate, to anchor the liquid crystal; and
step 5): releasing the voltage to obtain the liquid crystal display panel,
wherein the branched organosilicon material has a molecular formula shown in formula I, $$Si_nO_{2n+1}R^1{}_nR^2{}_{n+2}, \quad \text{formula I}$$

wherein $R^1$ is directly connected to a silicon atom, while $R^2$ is connected to a silicon atom via an oxygen atom, two adjacent silicon atoms being connected via an oxygen atom;
wherein n is an integer in the range from 2 to 15;
wherein $R^2$ is a $C_1$-$C_5$ alkyl; and
wherein $R^1$ is a group containing 10-30 carbon atoms, including at least one group selected from —$CR^3$=$CR^3$—, —C≡C—, $C_6$-$C_{20}$ arylene, $C_3$-$C_{15}$ cycloalkylene, —CONH—, and —COO—, one or more H atoms of $R^1$ being substituted by heteroatoms, wherein $R^3$ is hydrogen or a $C_1$-$C_3$ alkyl.

6. The method according to claim 5, wherein in step 2), the mixed solution contains 0.1-5 wt % of the branched organosilicon material.

7. The method according to claim 5, wherein in step 2), the reactive monomer comprises at least one selected from a group consisting of epoxy resin and fatty amine epoxy curing agent combination, acrylates and derivatives thereof, methyl acrylate and derivatives thereof, styrene and derivatives thereof;
wherein the mixed solution contains 0.01-0.1 wt % of the reactive monomer.

8. The method according to claim 5, wherein in step 4), the polymerization is a radiation polymerization, the voltage applied is in the range from 15 to 25 V.

9. The method according to claim 5, wherein in step 1), the first substrate and the second substrate are respectively a color filter substrate and a thin film transistor substrate.

10. The method according to claim 5, wherein n is an integer in the range from 2 to 10;
wherein $R^2$ is methyl, ethyl, or propyl;
wherein $R^1$ contains a group selected from —$CR^3$=$CR^3$—, —C≡C, phenylene, $C_3$-$C_6$ cycloalkylen, —CONH—, and —COO—, one or more H atoms in the phenyl or cycloalkylene being substituted with halogen atoms, wherein $R^3$ is hydrogen, methyl, or ethyl.

11. The method according to claim 5, wherein n is an integer in the range from 2 to 6;
wherein $R^2$ is methyl, ethyl or propyl; and
wherein $R^1$ is selected from the following groups:

—continued
—(CH$_2$)$_2$—CONH—HC=CH—COO—C$_8$H$_{17}$,

—(CH$_2$)$_2$—CONH—C$_4$H$_8$—COO—C$_6$H$_{13}$,

12. The method according to claim 5, wherein when n is 2, 3, or 4, the organosilicon material is shown in formula II, III, or IV:

formula II formula III formula IV

13. A liquid crystal display panel, comprising: a first substrate, a second substrate, a liquid crystal, a polymer, and a branched organosilicon material, wherein the branched organosilicon material has a molecular formula shown in formula I,

$$Si_nO_{2n+1}R^1{}_nR^2{}_{n+2}, \quad \text{formula I}$$

wherein $R^1$ is directly connected to a silicon atom, while $R^2$ is connected to a silicon atom via an oxygen atom, two adjacent silicon atoms being connected via an oxygen atom;
wherein n is an integer in the range from 2 to 15;
wherein $R^2$ is a $C_1$-$C_5$ alkyl; and
wherein $R^1$ is a group containing 10-30 carbon atoms, including at least one group selected from —$CR^3$=$CR^3$—, —C≡C—, $C_6$-$C_{20}$ arylene, $C_3$-$C_{15}$ cycloalkylene, —CONH—, and —COO—, one or more H atoms of $R^1$ being substituted by heteroatoms, wherein $R^3$ is hydrogen or a $C_1$-$C_3$ alkyl.

14. The liquid crystal display panel according to claim 13, wherein n is an integer in the range from 2 to 10;
wherein $R^2$ is methyl, ethyl, or propyl; and/or
wherein $R^1$ contains a group selected from —$CR^3$=$CR^3$—, —C≡C, phenylene, $C_3$-$C_6$ cycloalkylen, —CONH—, and —COO—, one or more H atoms in the phenyl or cycloalkylene being substituted with halogen atoms, wherein $R^3$ is hydrogen, methyl, or ethyl.

15. The liquid crystal display panel according to claim 13, wherein n is an integer in the range from 2 to 6;
wherein $R^2$ is methyl, ethyl or propyl; and
wherein $R^1$ is selected from the following groups:

16. The liquid crystal display panel according to claim 13, wherein when n is 2, 3, or 4, the organosilicon material is shown in formula II, III, or IV:

formula II formula III formula IV.

* * * * *